US007676051B2

(12) United States Patent
Fischer et al.

(10) Patent No.: US 7,676,051 B2

(45) Date of Patent: Mar. 9, 2010

(54) HEARING DEVICE AND CORRESPONDING METHOD FOR INSERTING THE HEARING DEVICE

(75) Inventors: Eghart Fischer, Schwabach (DE); Uwe Raβ, Nürnberg (DE)

(73) Assignee: Siemens Audiologische Technik GmbH, Erlangen (DE)

(*) Notice: Subject to any disclaimer, the term of this patent is extended or adjusted under 35 U.S.C. 154(b) by 1147 days.

(21) Appl. No.: 11/281,667

(22) Filed: Nov. 17, 2005

(65) Prior Publication Data

US 2006/0109995 A1 May 25, 2006

(30) Foreign Application Priority Data

Nov. 18, 2004 (DE) ........................ 10 2004 055 753

(51) Int. Cl.
*H04R 25/00* (2006.01)
*A61B 7/02* (2006.01)

(52) U.S. Cl. ........................................ 381/330; 181/135

(58) Field of Classification Search ................. 381/330; 181/135

See application file for complete search history.

(56) References Cited

U.S. PATENT DOCUMENTS

| | | | | |
|---|---|---|---|---|
| 5,046,580 | A * | 9/1991 | Barton | 181/135 |
| 6,600,825 | B1 | 7/2003 | Leysieffer | |
| 7,027,608 | B2 * | 4/2006 | Fretz et al. | 381/330 |
| 2003/0155173 | A1 * | 8/2003 | Widmer et al. | 181/135 |

FOREIGN PATENT DOCUMENTS

| | | | |
|---|---|---|---|
| DE | 78 30 156 | U | 4/1979 |
| DE | 44 26 967 | A1 | 2/1996 |
| DE | 198 58 399 | C2 | 7/2000 |
| EP | 1 463 375 | A2 | 9/2004 |
| WO | 2004073349 | A2 | 8/2004 |

* cited by examiner

*Primary Examiner*—Brian Ensey

(57) ABSTRACT

A linking element is provided for a hearing device, which connects the first behind-the-ear part and second behind-the-ear-part. In one embodiment the linking element is rigid. In another embodiment the linking element may be made of a memory material or have a spring component, so that the second behind-the-ear part is automatically pushed into the auditory canal. A helical groove around the second behind-the-ear part is also advantageous, thereby ensuring automatic_insertion into the auditory canal and also ventilation for an open fitting.

12 Claims, 2 Drawing Sheets

HEARING DEVICE AND CORRESPONDING METHOD FOR INSERTING THE HEARING DEVICE

CROSS REFERENCE TO RELATED APPLICATIONS

This application claims priority to the German application No. 10 2004 055 753.5, filed Nov. 18, 2004 which is incorporated by reference herein in its entirety.

FIELD OF INVENTION

The present invention relates to a hearing device with a behind-the-ear part (BTE), an in-the-ear part (ITE) and a linking element which connects the behind-the-ear part to the in-the-ear part. Furthermore the present invention relates to a corresponding method for inserting the hearing device into and/or onto an ear.

BACKGROUND OF INVENTION

Hearing devices consisting of an ITE part, which is mostly configured as a receiver, and a BTE part, have some advantages compared with purely BTE or ITE hearing devices. However a widespread problem with this design is that the ITE part can only be positioned deep in the auditory canal in a complex and difficult manner. It is mostly connected to the BTE part using a very flexible, thin, cable-like link, which also makes it difficult to hold. In most cases both hands are needed at the same time to position the hearing device correctly and this is far too demanding for the motor skills of many elderly hearing device wearers. In this instance one hand holds the BTE part and the other guides the ITE part into the auditory canal.

Furthermore, it may be unpleasant for a person to push a receiver deep into their own ear. Hearing device wearers thus often call on an acoustician for this procedure, which however reduces acceptance of such hearing devices.

SUMMARY OF INVENTION

If an open fitting is desired, the receiver must be positioned in the ear and/or auditory canal as freely as possible. For this purpose in most cases additional measures are required to hold the ITE part in position. A further disadvantage with open fitting is that the receiver must be relatively loose in the auditory canal. There is always the risk then that the receiver could unintentionally be inserted too deeply into the auditory canal or could slide out of the auditory canal.

Small fixing wires are therefore proposed for an open fitting and these are inserted into grooves of the auricle and thus correspondingly hold the ITE part in its position. Flexible ‘olives’ are proposed for a closed fitting, which hold the ITE part in the auditory canal by means of friction and surface pressure.

Publication DE 44 26 967 A1 relates to a hearing device with an ear adapter and a linking element which can be suspended over the ear between a housing arranged behind the ear during wear and the ear adapter. The linking element is made of a flexible element that remains in its respective bent position.

Publication DE 78 30 156 U1 describes a hearing device comprising a plastic tube with a metal wire for the acoustic conductor. Inserting the metal wire into the plastic tube makes insertion and removal of the hearing device easier for the user.

An electroacoustic converter for hearing devices for airborne noise emission into the outer auditory canal is described in the publication DE 198 58 399 C2. According to the invention the electroacoustic converter comprises a housing that is hermetically gastight all round, with the wall configured as a bendable membrane, which is activated to vibrate flexurally by a converter drive unit, which brings about airborne noise emission outside the converter housing.

Publication EP 1 463 375 A2 proposes integrating the acoustic conductor for the input of an acoustic/electric or an electric/acoustic converter in the shell of a hearing device. This allows the converter and the acoustic conductor to be integrated into the otoplastic such that optimal account can be made for the amount of space available and the acoustic conditions.

Despite the prior art described to date, the insertion of a hearing device comprising a BTE part and an ITE part is frequently experienced as difficult and unpleasant by the user.

An object of the present invention is thus to facilitate the insertion of a hearing device comprising a BTE part and an ITE part and to simultaneously provide for adequate fixing of the ITE part. A corresponding method for inserting the hearing device is also to be proposed.

According to the invention, this object is achieved by the claims.

In addition according to the invention a method is provided for inserting a hearing device made of a behind-the-ear part, an in-the-ear part and a rigid linking element connecting the behind-the-ear part to the in-the-ear part, by positioning the in-the-ear part at an auditory canal opening, rotating the complete hearing device about the axis of the auditory canal while engaging the in-the-ear part in the auditory canal and fixing the behind-the-ear part behind the auricle, with the in-the-ear part assuming a stable position further to a subsequent deformation.

This allows automatic self-positioning of the in-the-ear part. Advantageously such a hearing device with a rigid linking element can be easily held and thus also easily inserted. Furthermore, the ITE part is adequately fixed when the hearing device is inserted.

The ITE part, the BTE part and/or the linking element is preferably individually tailored to the anatomy of the hearing device wearer. This results in improved wearing comfort on the one hand and on the other hand in a securely fitting hearing device. In addition, there is no risk of damage to the eardrum if the ITE part is inserted too deeply.

With a particular development of the hearing device according to the invention, the ITE part features a sheath comprising a helical or spiral recess or protrusion on the periphery. The helical and/or spiral shape allows the ITE part to engage in the auditory canal by means of a rotational movement. If an open fitting is desired, the helical and/or spiral recess provides for a linking channel on the hearing device.

The ITE part can be made of a silicon-type material. This material is both comfortable to wear and also reduces the risk of sliding.

BRIEF DESCRIPTION OF THE DRAWING

The present invention is now described in more detail with reference to the drawings.

DETAILED DESCRIPTION OF INVENTION

The exemplary embodiment described below in further detail represents a preferred embodiment of the present invention.

Figure 1:
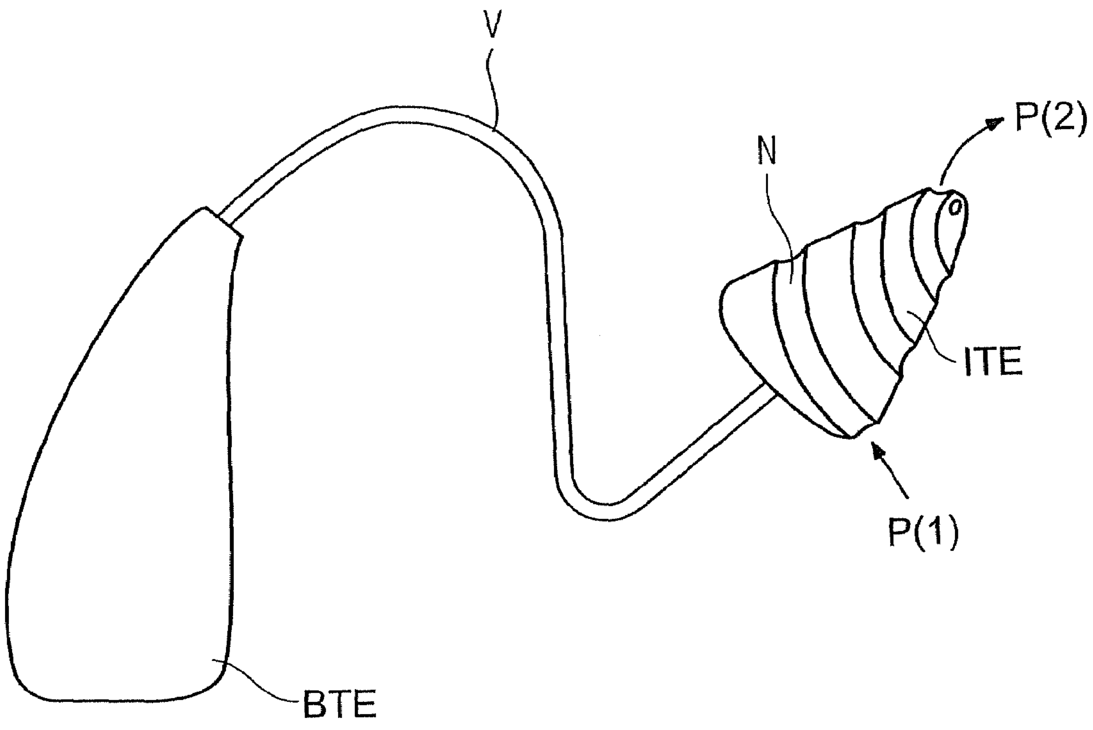
FIG. 1 shows a schematic view of a hearing device according to the invention.

Referring to FIG. 1, the hearing device shown in the figure is made up of a BTE part and an ITE part. In the present case the ITE part has a receiver.

Both the BTE part and the ITE part are connected to a rigid linking element V. This linking element V serves to transmit electrical signals from the BTE part to the receiver of the ITE part. Furthermore it serves to fix the hearing device to the auricle of the hearing device wearer. It also serves to insert the ITE part into the auditory canal since the ITE part can be easily guided and/or rotated by means of the rigid linking element V.

The linking element V has a wire for instance as a core and this is enclosed in a plastic along with an electrical linking line. The linking element V is essentially rigid and would be damaged in the event of deformation. Deformation is only possible for example when it is warm. By way of example, the mechanical characteristics of this linking element V thus correspond to those of spectacle arms.

The shape of the ITE part is advantageously precisely tailored to the auditory canal of the hearing device wearer. The BTE part should also be precisely matched to the space behind the ear. Furthermore the length and shape of the linking element V can be adjusted to the anatomy of the auricle of the hearing device wearer. This not only ensures the exact fit of the hearing device but also predefines the depth to which the ITE part can be inserted into the auditory canal.

The ITE part shown in the figure features a helical and/or spiral groove-like recess N on its periphery. On the one hand this serves to engage the ITE part in the auditory canal by means of a rotational movement. On the other hand the recess and/or groove N serve to ensure a channel past the ITE part, thereby ensuring an open fitting. An acoustic path P(1), P(2) and air path P(1). P(2) past the ITE part is therefore established, corresponding to the arrows shown in the figure.

The ITE part is made of a soft, flexible, skin-compatible material; a silicon-type substance is particularly suitable here.

The insertion process for such a hearing device is simple and comfortable for the hearing device wearer and can be outlined as follows: the completely rigid hearing device can be held firmly in one hand, e.g. at the bend of the rigid link between the BTE and ITE parts. The ITE part is first positioned in any manner in the ear and/or inserted to such a depth that it can no longer fall out. Normally gravity will then cause the BTE part to hang down. The second part of the insertion process then simply involves folding the hearing device behind the ear in a type of rotational movement. This rotational movement causes the helical ITE part to engage further in the auditory canal. This results in a type of locking mechanism which is linked to the insertion process. Such rotational insertion into the auditory canal is experienced as more pleasant and the wearer does not then have to push the hearing device into their own ear.

Assurance that the receiver is not inserted too far into the auditory canal is important for the hearing device wearer and represents a comfort factor which is not to be underestimated during insertion.

According to an alternative embodiment the core of the lining element V is made of a memory material. The linking element V thus resumes a predefined stable final shape after bending. This can be used in conjunction with the helical recesses N and/or protrusions of the ITE part. If the linking element V is twisted before insertion, it slowly reverts back to the stable final shape, thereby rotating the ITE part in relation to the BTE part. This reverse rotation can now be used to engage the ITE part in the auditory canal. This means that that ITE part automatically engages in the ear when the BTE part is fixed behind the auricle.

Figure 2:
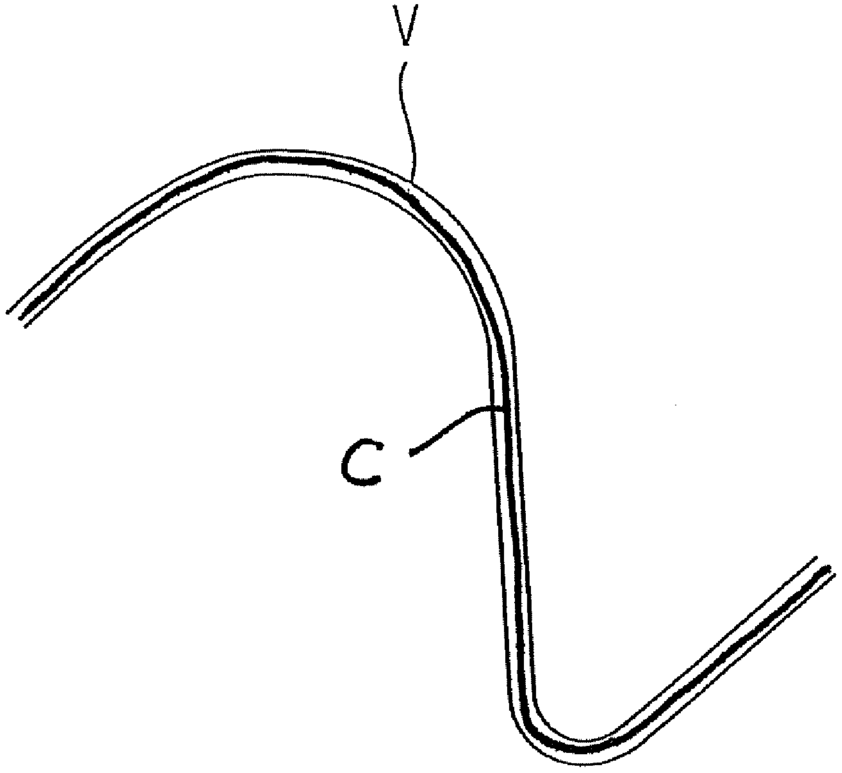
FIG. 2 shows a schematic view of the linking element with a spring wire used as the core of the linking element.

Referring to FIG. 2, further embodiment of the present invention features a linking element V having a spring (C). In the simplest of cases a spring wire (C) is used as the core of the linking element V. The spring linking element V is only given a basic shape when it is tailored to the hearing device wearer. When the BTE part is fixed behind the auricle, the ITE part is initially not yet located in its final position in the auditory canal but the spring linking element is taut. The spring force of the linking element V causes it to be gradually pushed deeper into the auditory canal. In particular chewing movements by the hearing device wearer can cause the ITE part to slide deeper into the auditory canal, thereby reaching its final position after a short time.

The proposed embodiments of the claimed hearing device thus ensure easy insertion. Furthermore they provide for secure and deep positioning of the ITE part in the auditory canal. Furthermore ventilation for open fitting can be ensured by the special embodiment of the ITE part.

The invention claimed is:

1. A hearing device, comprising:

a first part sized and configured to be worn behind an ear;

a second part sized and configured to be worn in an auditory canal of a user of the hearing device, a shape of the second part customized to the auditory canal of the user of the hearing device, the second part comprises a sheath having a helical or spiral recess, or a protrusion arranged on the periphery of the second part to allow the second part to engage in the auditory canal via a rotational movement of the second part; and a linking element connects the first part to the second part, the linking element comprising a memory material for ensuring a stable and predefined final shape of the linking element such that the linking element reverts back to the predefined final shape after bending.

2. A hearing device, comprising:

a first part sized and configured to be worn behind an ear;

a second part sized and configured to be worn in an auditory canal of a user of the hearing device, a shape of the second part customized to the auditory canal the user of the hearing device; and a linking element connects the first part to the second part, the linking element comprising a core material, the core material is a spring component for automatically pushing the second part into the auditory canal of the ear when the second part is worn in a preliminary position at the ear not yet corresponding to a final desired position of the second part within the auditory canal such that the second part automatically slides deeper into the auditory canal relative to the preliminary position.

3. The hearing device according to claim 1, wherein the first part is customized to the auditory canal of the user of the hearing device.

4. The hearing device according to claim 2, wherein the first part is customized to the auditory canal of the user of the hearing device.

5. The hearing device according to claim 2, wherein the second part comprises a sheath having a helical or spiral recess, or a protrusion arranged on the periphery of the second part to allow the second part to engage in the auditory canal via a rotational movement of the second part.

6. The hearing device according to claim 1, wherein the first part is made of a silicon-type material.

7. The hearing device according to claim 2, wherein the first part is made of a silicon-type material.

8. A method of inserting a hearing device into an auditory canal of an ear, the hearing device comprising:

a first part sized and configured to be worn behind a ear;

a second part sized and configured to be worn in the ear part; and a rigid linking element for connecting the first part to the second part, the method comprising:

positioning the second part at an opening of the auditory canal;

rotating the hearing device about a longitudinal axis of the auditory canal while engaging the second part into the auditory canal; and fixing the first part behind the auricle.

9. The method according to claim 8, wherein the second part comprises a sheath having a helical or spiral recess, or a protrusion arranged on the periphery of the second part such that the second part is inserted automatically into the auditory canal while rotating the hearing device using the helical or spiral recess, or the protrusion.

10. The hearing device according to claim 1, wherein a length and shape of the linking element is customized to the user to assure the second part is not inserted too far into the auditory canal of the user.

11. The hearing device according to claim 2, wherein a length and shape of the linking element is customized to the user to assure the second part is not inserted too far into the auditory canal of the user.

12. The hearing device according to claim 1, wherein the linking element provides for rotation of the second part into the auditory canal thereby automatically inserting the second part into the auditory canal when the linking element is bent from in predefined final shape order to fix the first part behind the ear.

* * * * *